(12) United States Patent
Conlan et al.

(10) Patent No.: US 11,738,075 B2
(45) Date of Patent: Aug. 29, 2023

(54) **METHOD FOR LYOPHILIZING LIVE VACCINE STRAINS OF *FRANCISELLA TULARENSIS***

(71) Applicant: NATIONAL RESEARCH COUNCIL OF CANADA, Ottawa (CA)

(72) Inventors: Joseph Wayne Conlan, Ottawa (CA); Kevan McRae, Ottawa (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 0 days.

(21) Appl. No.: 16/982,322

(22) PCT Filed: Mar. 20, 2019

(86) PCT No.: PCT/CA2019/050340
§ 371 (c)(1),
(2) Date: Sep. 18, 2020

(87) PCT Pub. No.: WO2019/178687
PCT Pub. Date: Sep. 26, 2019

(65) Prior Publication Data
US 2021/0008191 A1   Jan. 14, 2021

Related U.S. Application Data

(60) Provisional application No. 62/645,409, filed on Mar. 20, 2018.

(51) Int. Cl.
*A61K 39/02* (2006.01)
*A61K 9/00* (2006.01)
(Continued)

(52) U.S. Cl.
CPC ........ *A61K 39/0208* (2013.01); *A61K 9/0019* (2013.01); *A61K 9/19* (2013.01);
(Continued)

(58) Field of Classification Search
CPC .... C12N 15/102; C12N 2500/34; C12N 1/04; C12N 1/20; C12N 2500/42; Y02A 50/30;
(Continued)

(56) References Cited

U.S. PATENT DOCUMENTS 4,596,792 A   6/1986   Vyas
4,599,230 A   7/1986   Chisari et al.
(Continued)

FOREIGN PATENT DOCUMENTS

CA   3094404 A1 *   9/2019   ......... A61K 39/0208
EP   1123710 B1   8/2005
(Continued)

OTHER PUBLICATIONS

Baheti et al, J. Excipients and Food, 2010, 1(1):41-54 (Year: 2010).*
(Continued)

*Primary Examiner* — Jana A Hines
(74) *Attorney, Agent, or Firm* — BCF LLP

(57) ABSTRACT

There are provided compositions and methods for lyophilization and/or storage of live vaccine strains of *Francisella tularensis*. More specifically, there are provided lyophilization media and uses thereof for the preparation and long-term storage of *Francisella tularensis* vaccines.

13 Claims, 6 Drawing Sheets

(51) Int. Cl.
 *A61K 9/19* (2006.01)
 *C12N 1/20* (2006.01)
 *C12N 15/10* (2006.01)
 *A61K 39/00* (2006.01)

(52) U.S. Cl.
 CPC ............. *C12N 1/20* (2013.01); *C12N 15/102* (2013.01); *A61K 2039/522* (2013.01); *A61K 2039/54* (2013.01); *C12N 2500/34* (2013.01); *C12N 2500/42* (2013.01)

(58) Field of Classification Search
 CPC .... A61K 9/19; A61K 2039/54; A61K 9/0019; A61K 2039/522; A61K 39/0208; A61K 47/10; A61P 31/04; A61P 37/04
 See application file for complete search history.

(56) References Cited

U.S. PATENT DOCUMENTS

| | | | |
|---|---|---|---|
| 4,599,231 | A | 7/1986 | Chisari et al. |
| 4,601,903 | A | 7/1986 | Frasch |
| 5,792,643 | A | 8/1998 | Herrmann et al. |
| 7,910,351 | B2 * | 3/2011 | Sjostedt ............... C07K 14/195 424/234.1 |
| 8,673,357 | B2 * | 3/2014 | Truong-Le ............... B01D 1/18 34/293 |
| 8,993,302 | B2 * | 3/2015 | Conlan ................... A61P 31/04 424/234.1 |
| 10,736,848 | B2 * | 8/2020 | Von Andrian ............................... A61K 39/001156 |
| 10,828,340 | B2 * | 11/2020 | Jones ...................... A61K 35/38 |
| 11,045,555 | B2 * | 6/2021 | Zink ................. G01N 33/56983 |
| 11,179,339 | B2 * | 11/2021 | Fela .......................... C12N 1/04 |
| 11,224,647 | B2 * | 1/2022 | Horwitz ................. A61K 39/07 |
| 2005/0175630 | A1 * | 8/2005 | Raz .................... A61K 39/0208 424/203.1 |
| 2012/0308526 | A1 * | 12/2012 | Ohtake .................... B01D 1/18 424/94.4 |
| 2021/0008191 | A1 * | 1/2021 | Conlan .................. A61P 37/04 |

FOREIGN PATENT DOCUMENTS

| | | | | |
|---|---|---|---|---|
| RU | | 2549971 C1 * | 5/2015 | |
| WO | | 2000029018 A1 | 5/2000 | |
| WO | | 2010124377 A1 | 11/2000 | |
| WO | | 2010124377 A1 | 11/2010 | |
| WO | | 2010124428 A1 | 11/2010 | |
| WO | WO-2010124377 A1 * | 11/2010 | ............. C12N 9/104 |
| WO | | 2018027075 A1 | 2/2018 | |
| WO | WO-2019178687 A1 * | 9/2019 | ......... A61K 39/0208 |

OTHER PUBLICATIONS

Audran R. et al. Vaccine 21:1250-5, 2003.
Chamberlain, R.E., Appl. Microbiol. 1965, 13:232-5.
Conlan, J.W. et al., Vaccine 2010, 28(7): 1824-31.
Denis-Mize et al., Cell Immunol., 225:12-20, 2003.
Eigelsbach and Downs, J. Immunol. 1961, 87:415-425.
Eneslatt et al., Eur. J. Immunol. 2011, 41(4): 974-80.
Golovliov, I. et al., PLoS One 2013, 8(11): e78671.
Karlsson, J. et al., Microb. Comp. Genomics 2000, 5(1): 25-39.
Leslie et al., Appl. Environ. Microbiol. 1995, 61(10): 3592-3597.
Lindgren, H. et al., Infect. Immun. 2009, 77(10): 4429-36.
Marohn et al, Live attenuated tularemia vaccines: recent developments and future goals, Vaccine, 2013, 31(35): 1824-1831.
Ohtake et al., J. Pharm. Sci. 2011, 100(8): 3076-3087.
Pasetti et al., Vaccine 2008, 26(14): 1773-85.
Ryden, P. et al., Mol. Immunol. 2013, 54(1): 58-67.
Salomonsson, E. et al., Infect. Immun. 2009, 7: 3424-31.
Sandstrom, G. et al., J. Clin. Microbiol. 1987, 25(4): 641-4.
Saslaw et al, Tularemia vaccine study. II. Respiratory challenge, Archives of Internal Medicine, 1961, 107(5): 702-714.
Saslaw et al, Tularemia vaccine study. I. Intracutaneous challenge, Archives of Internal Medicine, 1961, 107(5): 689-701.
Shen, H. et al., PLoS One 2010, 5(10): e13349.
Sjostedt, A. et al., J. Immunol. 1990, 145(1): 311-7.
Streeter, J. Appl. Microbiol. 2003, 95: 484-491.
Twine, S.M. et al., Biochem. Biophys. Res. Comm. 2006, 346(3):999-1008.
Twine, S.M. et al., PLoS One 2010, 5(4): e10000.
Eigelsbach, H.T. et al., "Prophylactic effectiveness of live and killed tularemia vaccines", J. Immunol., 1961, vol. 87(4), pp. 415-425.
Ohtake, S. et al., "Formulaitation and stabilization of Francisella tularensis live vaccine strain", J. Pharm. Sci., Aug. 2011, vol. 100(8), pp. 3076-3087.
Marohn, M.E. et al., "Live attenuated tularemia vaccines: recent developments and future goals", Vaccine, Aug. 2, 2013, vol. 31(35), pp. 3485-3491.
Conlan, J.W. et al., "Differential ability of novel attenuated targeted delection mutants of Francisella tularensis subspecies tularensis strain SCHU S4 to protect mice against aerosol challenge with virulent bacteria: effects of host background and route of immunization", Vaccine, Feb. 17, 2010, vol. 28(7), pp. 1824-1831.
International Search Report and Written Opinion issued in corresponding International application No. PCT/CA2019/050340 dated Jun. 4, 2019.
Supplementary European Search Report issued in corresponding European patent application No. 19772499.0 dated Nov. 25, 2021.
Emami, F. et al., Drying technologies for the stability and bioavailability of biopharmaceuticals, Pharmaceutics 2018, 10, 131, Aug. 17, 2018.
Otero M.C. et al., Optimization of the freeze-drying media and survival throughout storage of freeze-dried Lactobacillus gasseri and Lactobacillus delbrueckii subsp. delbrueckii for veterinarian probiotic applications, Process Biochemistry 42 (2007) 1406-1411.
Appendix B, Vaccines, 2021.
Langford A. et al., Drying of biopharmaceuticals: Recent developments, new technologies and future direction, Japan Journal of Food Engeneering, vol. 19, No. 1, pp. 15-24, Mar. 2018.
Day, J.B. et al., Effect of dehydrated storage on the survival of Francisella tularensis in infant formula, Food Microbiology 26 (2009) 932-935.

* cited by examiner

FIG. 5A

* p<0.05 (Kruskal-Wallis with Tukey's correction for multiple comparisons

FIG. 5B

METHOD FOR LYOPHILIZING LIVE VACCINE STRAINS OF *FRANCISELLA TULARENSIS*

CROSS-REFERENCE TO RELATED APPLICATIONS

This application claims the benefit of priority from U.S. Provisional Application No. 62/645,409 filed Mar. 20, 2018, which is incorporated by reference herein in its entirety.

FIELD

The present disclosure provides a method for lyophilizing live vaccine strains of *Francisella tularensis*. More specifically, the disclosure relates to lyophilization medium and uses thereof for the preparation and long-term storage of *Francisella tularensis* vaccines.

BACKGROUND

*Francisella tularensis* is a facultative intracellular bacterial pathogen that causes a spectrum of diseases collectively called tularemia. Two subspecies, subsp. *tularensis* (type A) and subsp. *holarctica* (type B) are pathogenic for humans. Both subspecies can cause severe disease following infection via direct contact with infected animals, via various biting insects including mosquitoes and ticks, ingestion, inhibation, or inhalation. Regardless of route of entry, type B strains do not usually cause lethal infection. However, inhalation of small numbers of type A strains (<20 colony forming units) is associated with a 30-60% mortality rate if untreated. This is a likely scenario following a bioterrorist attack, since few clinicians are aware of the symptoms of tularemia, few clinical laboratories employ the type of culture medium required to grow the pathogen from human blood or tissues, and the most successful antibiotics against *F. tularensis* (gentamicin and doxycycline) are rarely prescribed for the 2-4 weeks needed to successfully treat tularemia. For these reasons there is great interest in developing vaccines that can prevent or ameliorate infection following inhalation of type A *F. tularensis*.

An empirically attenuated type B strain of *F. tularensis* developed more than 70 years ago, *F. tularensis* live vaccine strain (LVS), has been used to protect against exposure to virulent type A strains of the pathogen. In formal testing during the 1960s using human volunteers, LVS was shown to impart complete protection against transdermal challenge with the type A strain SCHU S4, though it afforded lesser protection against an aerosol challenge (Saslaw et al., Arch. Int. Med. 1961, 107: 689-714). It is the sole vaccine to have been formally shown to possess these properties. However, due to safety concerns, it has never been licensed by the U.S. Food and Drug Administration (FDA).

Genomic sequencing of clinical type A and type B strains of *F. tularensis* as well as LVS allowed identification of the genetic modifications in the vaccine strain. Much of the attenuation of LVS versus clinical type B strains appears to be due to defects in a pilus gene, pilA, and a gene (FTT0918/fupA) involved in iron acquisition (Salomonsson, E. et al., Infect. Immun. 2009, 7: 3424-31; Lindgren, H. et al., Infect. Immun. 2009, 77(10): 4429-36). LVS also contains multiple other mutations that, separately or collectively, contribute to its attenuation. LVS is known to elicit both an antibody response and a CD4+ and CD8+ T-cell response to several *F. tularensis* proteins (Twine, S. M. et al., Biochem. Biophys. Res. Comm. 2006, 346(3):999-1008; Twine, S. M. et al., PLoS One 2010, 5(4): e10000; Sandstrom, G. et al., J. Clin. Microbiol. 1987, 25(4): 641-4; Sjostedt, A. et al., J. Immunol. 1990, 145(1): 311-7). The antigens of LVS that are responsible for eliciting protective immunity are unknown; additionally, because LVS is a vaccine generated from a type B strain, virulence factors and other macromolecules unique to type A strains are missing. These facts render difficult the task of designing specific antigen-based vaccines. As a result of the above factors, there is currently no FDA approved vaccine for general use that can provide prophylactic protection against respiratory tularemia.

Previously, we reported on the development of new vaccine strains of *F. tularensis* based on inactivation of the clpB gene from a fully virulent type A strain (SCHU S4) (Conlan, J. W. et al., Vaccine 2010, 28(7): 1824-31; Shen, H. et al., PLoS One 2010, 5(10): e13349; Ryden, P. et al., Mol. Immunol. 2013, 54(1): 58-67) or type B strain (FSC200) (Golovliov, I. et al., PLoS One 2013, 8(11): e78671; see also International PCT Application Publication No. WO 2010/124377, the entire contents of which are hereby incorporated by reference). Mutant *F. tularensis* strains comprising an inactivated (e.g., deleted) clpB gene, compositions comprising such mutants, and methods of conferring immunity against *F. tularensis* in a host, comprising administering the described mutant *F. tularensis* strains, have been described (WO 2010/124377). However, although the described clpB mutants of *F. tularensis* have been shown to be useful as vaccines for conferring immunity against *F. tularensis* in a host, there is a need for methods and compositions for preparation and long-term storage of such vaccines. Such methods and reagents could allow a readily available, stockpiled vaccine that would facilitate mass vaccination campaigns under threat conditions.

Solid vaccine formulations generally have a marked decrease in molecular motion and hydrolytic cleavage, thus resulting in a biopharmaceutical product with superior stability and shelf life. Lyophilization (also known as freeze-drying) is a common method that has been used to dehydrate solutions containing biologically active reagents and to stabilize vaccines. It has been shown to be useful for long-term storage of bacterial vaccines, however the viability of LVS after freeze-drying has been poor (the loss of viable bacteria following lyophilization is up to 99%), indicating that *F. tularensis* LVS is difficult to lyophilize without significant immediate loss in viability (Ohtake, S. et al., J. Pharm. Sci. 2011, 100(8): 3076-87; Eigelsbach, H. T. et al., J. Immunol. 1961, 87: 415-25).

Eigelsbach and Downs (J. Immunol. 1961, 87:415-425) describe live and killed tularemia vaccines. LVS derived from the *F. tularensis holarctica* subspecies was lyophilized from a liquid medium consisting of 10% sucrose, 1.3% gelatin, 0.1% agar, and 0.85% saline. Upon reconstitution in water, viability decreased by 10-20-fold, with up to a further 2-fold loss following storage for 1 year at 5° C. Eneslatt et al. (Eur. J. Immunol. 2011, 41(4): 974-80) showed that this formulation retained its post-lyophilization viability and immunogenicity for more than 50 years when stored at −80° C.

More recently, LVS grown in fermenters to GMP standards was lyophilized in 10 mM phosphate buffer containing 10% sucrose and 1.3% gelatin (Pasetti et al., Vaccine 2008, 26(14): 1773-85). Pasetti et al. describe a toxicological and immunological analysis of LVS administered to rabbits in varying doses and by different routes. They demonstrate that a novel LVS vaccine formulation was safe and highly immunogenic during pre-clinical studies in rabbits. LVS was formulated in 10 mM potassium phosphate, 10% sucrose and 1.3% gelatin, lyophilized and stored until use at either 2-8° C. or −10 to −30° C., but viability losses following lyophilization or storage were not reported.

Leslie et al. (Appl. Environ. Microbiol. 1995, 61(10): 3592-3597) showed that addition of trehalose or sucrose to samples of two bacterial strains, *Escherichia coli* DH5α and *Bacillus thuringiensis* HD-1, before freeze-drying can increase the overall viability of the samples. Leslie et al. report that the increased tolerance to drying may result from the sugars' ability to lower the temperature of the dry membrane phase transition and maintain general protein structure in the dry state.

Streeter (J. Appl. Microbiol. 2003, 95: 484-491) describes the effect of trehalose on survival of *Bradyrhizobium japonicum* during desiccation. Streeter reports that adding trehalose during growth of the bacterium significantly improved survival following desiccation.

Ohtake et al. (J. Pharm. Sci. 2011, 100(8): 3076-3087) describe an optimized formulation for foam drying LVS comprising 30% trehalose, 5% gelatin, and 0.02% Pluronic F68 surfactant in 25 mM phosphate buffer at pH8.0. This foam drying formulation resulted in up to 10-fold decrease in viability, but essentially no further loss of viability following storage at 4° C. for 12 weeks. The formulation lost approximately 0.6 $\log_{10}$ at +25° C. and approximately 2 $\log_{10}$ after 6 weeks at +37° C. However, long-term storage of this formulation was not assessed. Moreover, for subcutaneous or intradermal injection the maximum amount of trehalose permitted by the US Food and Drug Agency is 2%, and clinical grade trehelose is relatively expensive.

SUMMARY

It is an object of the present invention to ameliorate at least some of the deficiencies present in the prior art. Embodiments of the present technology have been developed based on the inventors' appreciation that there is a need for methods and compositions for preparation and long-term storage of *Francisella tularensis* vaccines that will allow for their widespread production, storage and use.

In particular, the lyophilization medium provided herein is the first lyophilization medium shown to be capable of preserving a live vaccine strain of *F. tularensis* subspecies *tularensis*. Previous studies reported losses of at least 90% viability, and in some cases greater than 99% viability, of LVS after lyophilization. In contrast, there are provided herein methods and compositions for lyophilization of live vaccine strains of *F. tularensis* that can preserve viability sufficient to maintain usefulness as a vaccine (i.e., maintain immunogenicity) and can be stored long-term after lyophilization without significant further loss of viability. We report herein lyophilization media and methods that can result, in some cases, in only about 50% loss of viability after lyophilization and/or preservation of viability after long-term storage of up to 3 years.

Accordingly, in a first aspect there is provided a lyophilization medium comprising clinically acceptable excipients for long-term storage of *F. tularensis* live vaccine strains, such as *F. tularensis* ΔclpB mutants, in a lyophilized state. In some embodiments, the lyophilization medium is suitable for long-term storage of *F. tularensis*. In some embodiments, the lyophilization medium is suitable for clinical use in a subject, including clinical use in human subjects.

In an embodiment, the lyophilization medium comprises mannitol, a disaccharide, and gelatin in a weight ratio of about 1:about 1:about 0.25, respectively, wherein the disaccharide is selected from sucrose, trehalose, and a mixture of sucrose and trehalose. In one embodiment, the lyophilization medium comprises about 1% mannitol, about 1% disaccharide, and about 0.25% gelatin, wherein the disaccharide is selected from sucrose, trehalose, and a mixture of sucrose and trehalose. In one embodiment, the lyophilization medium comprises about 1% mannitol, about 1% disaccharide, and about 0.25% gelatin in a phosphate buffer, wherein the disaccharide is selected from sucrose, trehalose, and a mixture of sucrose and trehalose. In one embodiment, the phosphate buffer has a concentration of about 10 mM. In one embodiment, the phosphate buffer is a potassium phosphate buffer having a concentration of about 10 mM and a pH of about 7.2. In one embodiment, the lyophilization medium comprises 1% mannitol, 1% sucrose, and 0.25% gelatin in 10 mM potassium phosphate buffer pH 7.2.

In an embodiment, the lyophilization medium is suitable for lyophilization and long-term storage of live mutant *F. tularensis* strains wherein the clpB gene is inactivated. Such mutant strains may be attenuated. The mutant strain may be derived from any appropriate clinical strain of *F. tularensis*, such as, without limitation, a wild-type clinical strain of *F. tularensis* selected from the group consisting of SCHU S4, FSC033, FSC108, and FSC200. In some embodiments the mutant strain is a fully virulent strain type A strain or a type B strain. In some embodiments, the clpB gene is deleted, for example the *F. tularensis* strain may be SCHU S4 ΔclpB or FSC200 ΔclpB. In an embodiment, the mutant strain is CCUG deposit number CCUG 59672.

In an embodiment, the lyophilization medium is suitable for preserving viability and/or preserving immunogenicity of a live *F. tularensis* strain during lyophilization and/or during long-term storage in a lyophilized state. For example, viability and/or immunogenicity can be preserved after storage of the lyophilized *F. tularensis* strain at temperatures of +4° C. or lower for at least 3 months, for at least 1 year or for at least 3 years, and/or at temperatures of about −20° C. for at least 3 months, at least 1 year or for at least 3 years.

In an embodiment, the lyophilization medium can preserve lyophilized *F. tularensis* clpB mutants (e.g., ΔclpB mutants) at temperatures of +4° C. or lower for at least 1 year. In some embodiments, the lyophilization medium can preserve lyophilized *F. tularensis* clpB mutants (e.g., ΔclpB mutants) at temperatures of +4° C. or lower for at least 3 years. In some embodiments, the lyophilization medium can preserve lyophilized *F. tularensis* clpB mutants (e.g., ΔclpB mutants) at temperatures of about −20° C. for at least 1 year. In some embodiments, the lyophilization medium can preserve lyophilized *F. tularensis* clpB mutants (e.g., ΔclpB mutants) at temperatures of about −20° C. for at least 3 years.

In an embodiment, the lyophilization medium can preserve lyophilized *F. tularensis* clpB mutants (e.g., ΔclpB mutants) at temperatures of +4° C. or lower for up to 1 year. In some embodiments, the lyophilization medium can preserve lyophilized *F. tularensis* clpB mutants (e.g., ΔclpB mutants) at temperatures of +4° C. or lower for up to 3 years. In some embodiments, the lyophilization medium can preserve lyophilized *F. tularensis* clpB mutants (e.g., ΔclpB mutants) at temperatures of about −20° C. for up to 1 year. In some embodiments, the lyophilization medium can preserve lyophilized *F. tularensis* clpB mutants (e.g., ΔclpB mutants) at temperatures of about −20° C. for up to 3 years.

In some embodiments, the lyophilization medium can preserve viability and/or immunogenicity of the lyophilized *F. tularensis* strain for at least about 5×, at least about 10×, at least about 15×, or at least about 20× longer than a medium consisting of 10% sucrose and 1.3% gelatin in a 10 mM potassium phosphate solution, such as the medium used to lyophilize LVS described in Pasetti et al., Vaccine 2008, 26(14): 1773-85.

In some embodiments, viability and/or immunogenicity of the lyophilized *F. tularensis* strain after storage is at least 30%, at least 40%, at least 50%, at least 60%, at least 70%, at least 80%, at least 90%, at least 95%, or at least 99% of initial post-lyophilization viability of the lyophilized *F. tularensis* strain.

In some embodiments, viability and/or immunogenicity of the lyophilized *F. tularensis* strain after storage is substantially unchanged compared to the strain's initial post-lyophilization viability.

In some embodiments, the lyophilization medium can preserve viability and/or immunogenicity of the *F. tularensis* strain during lyophilization such that the initial post-lyophilization viability and/or immunogenicity of the strain is at least about 35%, at least about 40%, at least about 45%, at least about 50%, at least about 55%, or at least about 60% of the pre-lyophilization viability.

In an embodiment, the lyophilization medium can preserve viability and/or immunogenicity of the *F. tularensis* strain such that no more than about 40% or about 50% of viability is lost after lyophilization compared to viability pre-lyophilization, and the viability and/or immunogenicity remains stable for at least 1 year after storage at +4° C. or below or at least 3 years after storage at −20° C. or below. In an embodiment, the lyophilization medium can preserve viability of the *F. tularensis* strain such that there is no more than about 2-fold loss of viability after lyophilization compared to viability pre-lyophilization (in other words, viability after lyophilization is about 50% of viability pre-lyophilization).

In some embodiments, the lyophilization medium can preserve viability and/or immunogenicity of the lyophilized *F. tularensis* strain when lyophilized at low concentrations of bacteria, for example at 1 vaccine dose/vial (~$10^7$ CFU/vial).

In a second aspect, there is provided a method for lyophilizing a live vaccine strain of *Francisella tularensis* (*F. tularensis*), comprising the steps of: 1) pelleting a culture of the live vaccine strain by centrifugation; 2) resuspending the live vaccine strain in the lyophilization medium provided herein; and 3) freeze-drying the resuspended live vaccine strain, thereby obtaining a lyophilized vaccine strain. The strain may be, for example, a mutant strain wherein the clpB gene is inactivated such as, without limitation, SCHU S4 ΔclpB or FSC200 ΔclpB.

In some embodiments, particularly where large cultures are used (e.g., cultures of 25 liters or more), diafiltration, tangential-flow filtration, or other art-recognized methods may be used to exchange the culture medium with the lyophilization medium in place of the step (1) above of pelleting the culture. It should be understood that the method used to suspend the strain in the lyophilization medium in preparation for freeze-drying is not meant to be particularly limited, and many such methods are known in the art. Similarly, the live vaccine strain may be resuspended in a volume of lyophilization medium equal to the initial volume of the culture or smaller or greater than the initial volume, and the culture may or may not be diluted prior to exchange with lyophilization medium; such steps will be determined by the person of skill in the art based on art-recognized techniques.

In some embodiments, the method further comprises a step of storing the lyophilized vaccine strain at a temperature of about +4° C. or below or at a temperature of about −20° C. or below, e.g., for several months, for at least one year, or for at least three years. In some embodiments, the method further comprises a step of storing the lyophilized vaccine strain at a temperature of about +4° C. or below or at a temperature of about −20° C. or below, e.g., for several months, for about one year, or for about three years.

In one embodiment, the lyophilized vaccine strain is stored for at least 1 year or at least 3 years at a temperature of about +4° C. or below or at a temperature of about −20° C. or below, and viability of the lyophilized vaccine strain after storage is at least about 30%, at least about 40%, at least about 50%, at least about 60%, at least about 70%, at least about 80%, at least about 90%, at least about 95%, or at least about 99% of the initial post-lyophilization viability of the lyophilized vaccine strain.

In some embodiments, the methods provided herein preserve viability and/or immunogenicity of the lyophilized vaccine strain after lyophilization and/or after storage, as described herein. In an embodiment, the lyophilized vaccine strain is capable of inducing an immune response against and/or conferring immunity against *F. tularensis* (e.g., virulent type A *F. tularensis*) in a subject (e.g., an animal or a human) after administration thereto.

In some embodiments, the methods and compositions provided herein can preserve the viability of an *F. tularensis* ΔclpB mutant, e.g., *F. tularensis* SCHU S4 ΔclpB, *F. tularensis* FSC200 ΔclpB by at least 5-fold, at least 10-fold, at least 15-fold, or at least 20-fold more than previously known lyophilization media, including lyophilization media historically used to manufacture LVS (such as, without limitation, media comprising 10% sucrose and 1.3% gelatin).

In some embodiments, *F. tularensis* strain is lyophilized at low concentrations, for example at 1 vaccine dose/vial (~$10^7$ CFU/vial). In other embodiments, the *F. tularensis* strain is lyophilized at concentrations of about 100 vaccine doses/vial or about 500 vaccine doses/vial.

In a third aspect, there is provided a vaccine for the prevention or treatment of *F. tularensis* infection and/or tularemia in a subject comprising the lyophilized vaccine strain produced according to the methods provided herein and/or using the lyophilization medium provided herein. The lyophilized vaccine strain may be reconstituted in a pharmaceutically-acceptable diluent, carrier, or excipient. Such a vaccine may be administered, for example, intradermally, intranasally, subcutaneously, by scarification, intramuscularly, orally, by aerosol or by inhalation, to an animal or a human subject.

In a fourth aspect, there is provided a method of inducing an immune response against and/or conferring immunity against *F. tularensis* in a subject, comprising administering a mutant *F. tularensis* strain wherein the clpB gene is inactivated to the subject, wherein the mutant *F. tularensis* strain comprises the lyophilized vaccine strain produced according to the methods provided herein and/or using the lyophilization medium provided herein. In one embodiment, the method induces an immune response against and/or confers immunity against virulent type A *F. tularensis* in the subject.

In a fifth aspect, there is provided a method of preventing, ameliorating or treating tularemia in a subject, comprising administering a mutant *F. tularensis* strain wherein the clpB gene is inactivated to the subject, wherein the mutant *F. tularensis* strain comprises the lyophilized vaccine strain produced according to the methods provided herein and/or using the lyophilization medium provided herein, such that tularemia is prevented, ameliorated or treated in the subject.

In another aspect, there is provided use of the lyophilization medium provided herein in the manufacture of a vaccine for prevention or treatment of *F. tularensis* infection. Use of the lyophillized vaccine strain produced according to the methods provided herein and/or using the lyophilization medium provided herein in the manufacture of a vaccine for prevention or treatment of *F. tularensis* infection is also provided.

In some embodiments, the methods and compositions provided herein may improve the storage and/or heat stability of *F. tularensis* vaccines. Such improved stability may provide one or more of the following advantages: 1) mitigating risks of vaccine potency loss during long-term storage, shipping, or distribution; 2) allowing for stockpiling in preparation for biological threat; 3) mitigating risks of vaccine potency loss during delivery to geographical areas with warm climates; and 4) allowing development and production of a commercially viable ΔclpB vaccine against tularemia that meets FDA licensing standards.

In another aspect there is provided a method for lyophilizing a live vaccine strain of *F. tularensis* comprising the steps of: 1) thawing a concentrated frozen liquid preparation of a live vaccine strain, the concentrated frozen liquid preparation comprising a growth medium or the lyophilization medium of any one of claims 1 to 3; 2) if the concentrated frozen liquid preparation comprises the growth medium, substantially removing the growth medium and resuspending the vaccine strain in the lyophilization medium of any one of claims 1 to 3; and 3) freeze-drying the vaccine strain in the lyophilization medium, thereby obtaining a lyophilized vaccine strain.

In some embodiments, the concentrated frozen liquid preparation comprises the growth medium. In some embodiments, the growth medium is modified casein partial hydrolysate medium (MCPH) or Chamberlain's Defined Medium (CDM). In some embodiments, the live vaccine strain is derived from a wild-type clinical strain of *F. tularensis* selected from the group consisting of SCHU S4, FSC033, FSC108, and FSC200. In some embodiments, the method further comprises diluting the vaccine strain to a single dose per container in the lyophilization medium prior to freeze-drying. In some embodiments, the vaccine is diluted to a single dose of about $10^7$ CFU per container.

Additional aspects and advantages of the present invention will be apparent in view of the following description. The detailed description and examples, while indicating particular embodiments of the invention, are given by way of illustration only, as various changes and modifications within the scope of the invention will become apparent to those skilled in the art in light of the teachings of this invention.

BRIEF DESCRIPTION OF THE DRAWINGS

For a better understanding of the invention and to show more clearly how it may be carried into effect, reference will now be made by way of example to the accompanying drawings, which illustrate aspects and features according to preferred embodiments of the present invention, and in which:

FIG. 5A shows skin reacogenicity at immunization site observed in BALB/c mice immunized intradermally with 1×10⁵ CFU of ΔclpB lyophilized for 3 years and stored at +4° C., −20° C., or −80° C. * denotes p<0.5 (Kruskal-Wallis with Tukey's correction for multiple comparisons). FIG. 5B shows the *Francisella* Skin Reaction Score Chart used for scoring.

DETAILED DESCRIPTION

Definitions

Figure 1:
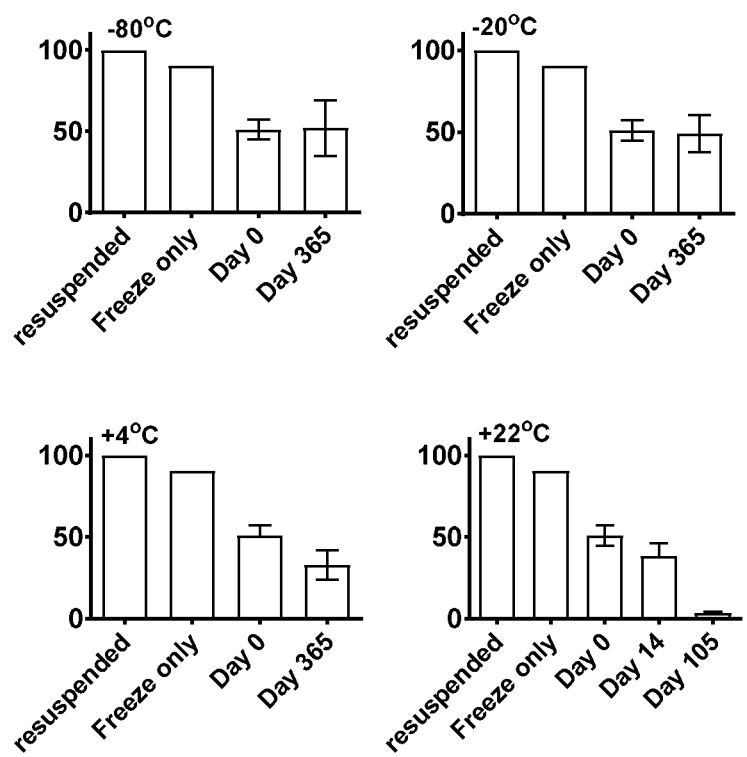
FIG. 1 shows viability of lyophilized samples stored at various temperatures for various amounts of time. SCHU S4ΔclpB bacteria were grown in modified casein partial hydrolysate (MCPH) broth, pelleted by centrifugation and resuspended and lyophilized in lyophilization medium (10 mM potassium phosphate buffer containing 1% mannitol, 1% sucrose and 0.25% gelatin, final pH7.2) at about $10^{10}$ colony forming units (CFU). These vials were stored at ambient (~22° C.), refrigerator (+4° C.), or freezer (−20° C. or −80° C.) temperatures, as indicated. At various times, as indicated, sample vials were thawed, lyophilized material was solubilized in water, and plated in order to determine viability. The determined % viability (CFU count after reconstitution/CFU count pre-lyophilization×100) is shown in the figure.

As used herein, the singular forms "a", "an" and "the" include plural references unless the content clearly dictates otherwise.

As used herein, the term "about" refers to a value that is within the limits of error of experimental measurement or determination. For example, two values which are about 1%, about 2%, about 3%, about 5%, about 10%, about 15%, or about 20% apart from each other, after correcting for standard error, may be considered to be "about the same" or "similar". In some embodiments, "about" refers to a variation of ±20%, ±10%, ±5%, ±3%, ±2% or ±1% from the specified value, as appropriate to perform the disclosed methods or to describe the disclosed compositions and methods, as will be understood by the person skilled in the art.

By the term "attenuation" or "attenuated", it is meant that a pathogen is kept alive, but exhibits reduced virulence such that it does not cause the disease caused by the virulent pathogen. The attenuation of a particular strain may result from e.g. the inactivation of the clpB gene, or may be the result of other mechanisms for attenuation, for example and not limited to mutagenesis, deletion or inactivation of targeted genes, or natural attenuation, or a combination thereof.

By the term "virulent *F. tularensis* strain" is meant a strain that may cause any disease in the spectrum referred to as tularemia, whether mild or severe. Non-limiting examples of virulent *F. tularensis* strains include SCHU S4, FSC033, FSC108, and FSC200. In some embodiments, a mutant *F. tularensis* strain may have additional mutations introduced to further attenuate the pathogen (either partially or completely) or for other purpose.

It should be understood that the methods and compositions provided herein can be used for preparation and/or storage of *F. tularensis* mutants, including *F. tularensis* mutants with inactivated clpB. In some embodiments, *F. tularensis* mutants are strains in which the clpB gene has been deleted (ΔclpB mutants). In some embodiments, an *F. tularensis* ΔclpB mutant is a virulent type A strain (e.g., SCHU S4). In some embodiments, an *F. tularensis* ΔclpB mutant is a type B strain (e.g., FSC200).

In an embodiment, the *F. tularensis* mutant strain is SCHU S4 ΔclpB, such as without limitation the strain deposited with the Culture Collection University of Gothenburg (CCUG; Sahlgrenska Academy of the University of Gothenburg, Box 7193, SE-402 34, Gothenburg, Sweden) and granted accession number CCUG 59672.

A gene may be "inactivated" by any suitable manner known in the art. For example, and not wishing to be limiting, the clpB gene may be inactivated using methods known in the art, for example by its complete or partial deletion from the *F. tularensis* strain, by an inactivation mutation such as a multiple nucleotide substitution, or by an inactivating insertion such as a transposon insertion. Further, inactivation of the clpB gene may result in complete or partial attenuation of a mutant *F. tularensis* strain.

"Lyophilization", also known as "freeze-drying", is a process used for preserving biological material such as vaccines, bacteria, and proteins, by removing the water from the sample, which typically involves first freezing the sample and then drying it, under a vacuum, at very low temperatures. Lyophilization methods are well-known in the art. It should be understood that any standard lyophilization procedures known in the art may be used with the compositions and methods provided herein; it is within the capabilities of persons of skill in the art to select procedures for lyophilization.

As used herein, the terms "lyophilization medium" and "lyophilization matrix" are used interchangeably to refer to a composition in which samples (e.g., bacteria) are suspended before being subjected to the freeze drying process. Bacteria are generally resuspended in a lyophilization medium prior to lyophilization using standard procedures, as are known in the art. Typically a suitable lyophilization medium for bacteria will help maintain their viability through the freeze drying process and subsequent storage, for example by stabilizing the cells and/or helping to retain structure of biomolecules.

As used herein, "viability" refers to the number of live bacteria or the percentage of live vs. dead bacteria in a sample prior to freezing, after freezing but prior to lyophilization, or after lyophilization and storage for periods of up to 3 years. Viability is often provided as a percentage, referring to the percentage of bacteria in a sample that are live after treatment (e.g., freezing or lyophilizing) compared to the number of viable bacteria before any such treatment. Alternatively, viability may be provided herein as the number of colony forming units (CFU) in a treated sample divided by the CFU prior to any such treatment. Many methods for determining viability of a bacterial sample are known in the art and any art-recognized technique or assay may be used. In some embodiments, post-lyophilization viability is determined as the CFU count after reconstitution/ CFU count pre-lyophilization×100.

The terms "preservation of viability" and "stability of viability" are used herein to mean that viability is substantially unchanged. As used herein, "substantially unchanged" viability means that the viability is approximately the same, e.g., within about 10% or about 20% of starting values, or that there is a loss of no more than about 0.5 $\log_{10}$ CFU, about 1 $\log_{10}$ CFU, or about 2 $\log_{10}$ CFU. In some embodiments, in the context of a vaccine, "substantially unchanged" viability means that viability is maintained at a sufficient level for usefulness as a vaccine, e.g., that immunogenicity is maintained. Preservation of a certain level of viability means that a certain level of viable cells is maintained in a sample relative to the level of viable cells present at a starting point, for example before a treatment (e.g. lyophilization) and/or before the passage of time. For example, preservation of 50% viability means that at least 50% of the cells in the sample remain alive, relative to the number of cells alive at a starting point. Preservation of viability after lyophilization may be assessed by assessing the viability of the culture after lyophilization in comparison to the viability of the culture immediately prior to lyophilization. Preservation of viability after lyophilization means that the viability of the culture is a given percentage, or higher, of the viability of the culture immediately prior to lyophilization. For example, preservation of viability of 35% means that 35% of cells remain alive after lyophilization relative to the starting population of viable cells immediately prior to lyophilization. As another example, if the initial viability of a sample immediately after lyophilization is 80%, relative to the viability of the sample immediately prior to lyophilization, then preservation of 50% viability at a given timepoint means that viability of at least 40%, relative to the viability of the sample immediately prior to lyophilization, is maintained in the sample at that timepoint.

In the context of an *F. tularensis* strain or a vaccine, "stability" means that immunogenicity is maintained and/or that viability is substantially unchanged, e.g., that the bacterial titer is sufficient for effective use as a vaccine against tularemia in a subject.

As used herein, "long-term" storage is used to refer to storage for an extended period of time. Without intending to limit the term, it generally refers to storage for at least several months (e.g., about or at least 2 months, about or at least 3 months, about or at least 6 months), or about or at least one year, about or at least two years, about or at least three years, or longer.

Pharmaceutical Compositions and Methods

There are provided herein compositions and methods for the prevention or amelioration of tularemia in a subject comprising *F. tularensis* strains prepared and/or stored as described herein. Compositions and methods for inducing an immune response to *F. tularensis* are also provided. Methods provided herein comprise administration of a live *F. tularensis* strain prepared and/or stored as described herein to a subject in an amount effective to induce an immune response against *F. tularensis*, thereby reducing, eliminating, ameliorating or preventing tularemia. Compositions and methods provided may also be used for the generation of antibodies for use in passive immunization against tularemia and treatment thereof.

A *F. tularensis* strain prepared and/or stored using the compositions and methods provided herein may thus be used to vaccinate a subject, administered to a subject to prevent or treat tularemia, etc., as described further herein. It will be understood by the person skilled in the art that a lyophilized strain provided herein will generally be reconstituted to liquid form prior to administration to a subject. For example, a lyophilized strain may be reconstituted in a pharmaceutically acceptable carrier, diluent or excipient, and/or in lyophilization medium, suitable for administration. It should be understood that reference to administration or use of a lyophilized strain herein is meant to include administration or use of a strain that was lyophilized and/or stored in a lyophilized state as described herein, and has been reconstituted in a form suitable for administration. In an embodiment, a lyophilized strain provided herein is reconstituted in water prior to administration to a subject.

Similarly, the dosage for administration will be dependent on various factors, including the size of the subject and the specifics of the composition formulated, and as discussed further below. Based on experience with LVS, and without wishing to be limiting in any manner, a dose of approximately $10^7$ CFU may in some cases be used for administration to humans. It would be within the capabilities of persons of skill in the art to determine appropriate dosages for vaccination.

The terms "subject" and "patient" are used interchangeably herein to refer to a subject in need of prevention for tularemia. A subject may be a vertebrate, such as a mammal, e.g., a human, a non-human primate, a rabbit, a rat, a mouse, a cow, a horse, a goat, or another animal. Animals include all vertebrates, e.g., mammals and non-mammals, such as mice, sheep, dogs, cows, avian species, ducks, geese, pigs, chickens, amphibians, and reptiles. In an embodiment, a subject is a human.

"Treating" or "treatment" refers to either (i) the prevention of infection or reinfection, e.g., prophylaxis, or (ii) the reduction or elimination of symptoms of the disease of interest, e.g., therapy. "Treating" or "treatment" can refer to the administration of a composition comprising a *F. tularensis* vaccine strain prepared and/or stored as described herein, or to the administration of antibodies raised against these *F. tularensis* vaccine strains. Treating a subject can prevent or reduce the risk of infection and/or induce an immune response to *F. tularensis*.

Treatment can be prophylactic (e.g., to prevent or delay the onset of the disease, to prevent the manifestation of clinical or subclinical symptoms thereof, or to prevent recurrence of the disease) or therapeutic (e.g., suppression or alleviation of symptoms after the manifestation of the disease). "Preventing" or "prevention" refers to prophylactic administration or vaccination with a *F. tularensis* vaccine strain prepared and/or stored as described herein or compositions thereof in a subject who has not been infected or who is symptom-free and/or at risk of infection.

As used herein, the term "immune response" refers to the response of immune system cells to external or internal stimuli (e.g., antigens, cell surface receptors, cytokines, chemokines, and other cells) producing biochemical changes in the immune cells that result in immune cell migration, killing of target cells, phagocytosis, production of antibodies, production of soluble effectors of the immune response, and the like. An "immunogenic" molecule is one that is capable of producing an immune response in a subject after administration.

"Active immunization" refers to the process of administering an antigen (e.g., an immunogenic molecule, e.g., a *F. tularensis* vaccine strain described herein) to a subject in order to induce an immune response. In contrast, "passive immunization" refers to the administration of active humoral immunity, usually in the form of pre-made antibodies, to a subject. Passive immunization is a form of short-term immunization that can be achieved by the administration of an antibody or an antigen-binding fragment thereof. Antibodies can be administered in several possible forms, for example as human or animal blood plasma or serum, as pooled animal or human immunoglobulin, as high-titer animal or human antibodies from immunized subjects or from donors recovering from a disease, as polyclonal antibodies, or as monoclonal antibodies. Typically, immunity derived from passive immunization provides immediate protection or treatment but may last for only a short period of time.

As used herein, "tularemia" refers to all *F. tularensis*-associated diseases, i.e., diseases caused by *F. tularensis* infection.

In some embodiments, there are provided compositions and methods for active immunization against tularemia. Compositions and methods are provided for inducing an immune response to *F. tularensis* bacteria in a subject, comprising administering to the subject a *F. tularensis* vaccine strain prepared and/or stored as described herein, optionally in the presence of an adjuvant, in an amount effective to induce an immune response in the subject. In one embodiment, there is provided a composition comprising an effective immunizing amount of a *F. tularensis* vaccine strain as provided herein and an adjuvant, wherein the composition is effective to prevent or treat tularemia in a subject in need thereof. In an embodiment, an adjuvant is not required, i.e., compositions and methods are provided for inducing an immune response to *F. tularensis* bacteria in a subject, comprising administering to the subject an *F. tularensis* vaccine strain as provided herein and a pharmaceutically acceptable carrier, excipient, or diluent, in an amount effective to induce an immune response in the subject.

Adjuvants generally increase the specificity and/or the level of immune response. An adjuvant may thus reduce the quantity of antigen necessary to induce an immune response, and/or the frequency of injection necessary in order to generate a sufficient immune response to benefit the subject. Any compound or compounds that act to increase an immune response to an antigen and are suitable for use in a subject (e.g., pharmaceutically-acceptable) may be used as an adjuvant in compositions, vaccines, and methods of the invention. In some embodiments, the adjuvant may be the carrier molecule (for example, but not limited to, cholera toxin B subunit, liposome, etc.) in a conjugated or recombinant antigen. In alternative embodiments, the adjuvant may be an unrelated molecule known to increase the response of the immune system (for example, but not limited to attenuated bacterial or viral vectors, AMVAD, etc.). In one embodiment, the adjuvant may be one that generates a strong mucosal immune response such as an attenuated virus or bacteria, or aluminum salts.

Examples of an adjuvant include, but are not limited to, cholera toxin, *E. coli* heat-labile enterotoxin, liposome, immune-stimulating complex (ISCOM), immunostimulatory sequences oligodeoxynucleotide, and aluminum hydroxide. The composition can also include a polymer that facilitates in vivo delivery (See, e.g., Audran R. et al. Vaccine 21:1250-5, 2003; and Denis-Mize et al., Cell Immunol., 225:12-20, 2003). Other suitable adjuvants are well-known to those of skill in the art. Alternatively, in some embodiments, *F. tularensis* vaccine strains as provided herein are used in vaccines against tularemia without additional adjuvant.

*F. tularensis* vaccine strains as provided herein may be combined with a pharmaceutically acceptable carrier, diluent or excipient to form a pharmaceutical composition suitable for administration to a subject. Pharmaceutically acceptable carriers can include a physiologically acceptable compound that acts to, e.g., stabilize, or increase or decrease the absorption or clearance rate of a pharmaceutical composition. Generally, a pharmaceutically acceptable carrier must be compatible with the active ingredient of the composition, optionally capable of stabilizing the active ingredient, and not deleterious to the subject to be treated. Physiologically acceptable compounds can include, e.g., water, phosphate buffered saline, a bicarbonate solution, carbohydrates, such as glucose, sucrose, or dextrans, antioxidants, such as ascorbic acid or glutathione, chelating agents, low molecular weight proteins, compositions that reduce the clearance or hydrolysis of glycopeptides, or excipients or other stabilizers and/or buffers. Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. Detergents can also be used to stabilize or to increase or decrease the absorption of the pharmaceutical composition, including liposomal carriers. Pharmaceutically acceptable carriers and formulations are known to the skilled artisan and are described in detail in the scientific and patent literature, see e.g., the latest edition of Remington's Pharmaceutical Science, Mack Publishing Company, Easton, Pa. ("Remington's"). One skilled in the art would appreciate that the choice of a pharmaceutically acceptable carrier, diluent or excipient including a physiologically acceptable compound depends, for example, on the mode and route of administration of the vaccine, composition, or bacterial strain of the invention, and on its particular physio-chemical characteristics. In some embodiments, lyophilized *F. tularensis* vaccine strains as provided herein are combined with water to form a pharmaceutical composition suitable for administration to a subject.

Compositions and vaccines of the present invention may be administered by any suitable means, for example, orally, such as in the form of pills, tablets, capsules, granules or powders; sublingually; buccally; parenterally, such as by subcutaneous, intradermal, intranasal, intravenous, intramuscular, intraperitoneal or intrasternal injection or using infusion techniques (e.g., as sterile injectable aqueous or non-aqueous solutions or suspensions); nasally, such as by inhalation spray, aerosol, mist, or nebulizer; topically, such as in the form of a cream, ointment, salve, powder, or gel; transdermally, such as in the form of a patch; transmucosally; or rectally, such as in the form of suppositories. The present compositions may also be administered in a form suitable for immediate release or extended release. Immediate release or extended release may be achieved by the use of suitable pharmaceutical compositions, or, particularly in the case of extended release, by the use of devices such as subcutaneous implants or osmotic pumps.

In some embodiments, pharmaceutical compositions described herein may be administered parenterally, e.g., by subcutaneous or intradermal or intramuscular injection, or using other modes of administration such as suppositories and oral formulations. For suppositories, binders and carriers may include, for example, polyalkalene glycols or triglycerides. Oral formulations may include normally employed incipients such as pharmaceutical grades of saccharine, cellulose, magnesium carbonate and the like. These compositions may take the form of solutions, suspensions, tablets, pills, capsules, sustained release formulations, or powders. Compositions may be prepared as final products for injections, as liquid solutions, or emulsions, for example (See, e.g., U.S. Pat. Nos. 4,601,903; 4,599,231; 4,599,230; and 4,596,792).

It is often advantageous to formulate oral or parenteral compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic or immunogenic effect in association with the required pharmaceutical carrier. The dosage unit may be housed within a container, such as a vial, bottle, or ampoule.

In an embodiment, a composition or vaccine is prepared as an injectable, either as a liquid solution or suspension, or as a solid form which is suitable for solution or suspension in a liquid vehicle prior to injection. In another embodiment, a composition or vaccine is prepared in solid form, emulsified or encapsulated in a liposome vehicle or other particulate carrier used for sustained delivery. For example, a vaccine can be in the form of an oil emulsion, a water-in-oil emulsion, a water-in-oil-in-water emulsion, a site-specific emulsion, a long-residence emulsion, a sticky emulsion, a microemulsion, a nanoemulsion, a liposome, a microparticle, a microsphere, a nanosphere, or a nanoparticle. A vaccine may include a swellable polymer such as a hydrogel, a resorbable polymer such as collagen, or certain polyacids or polyesters such as those used to make resorbable sutures, that allow for sustained release of a vaccine.

It will be understood that the specific dose level and frequency of dosage for any particular subject may be varied and may depend upon a variety of factors including the activity of the specific compound employed, the metabolic stability and length of action of that compound, the species, age, body weight, general health, sex and diet of the subject, the mode and time of administration, rate of excretion and clearance, drug combinations, and severity of the particular condition.

Kits

Kits are provided for preventing or treating tularemia, comprising one or more *F. tularensis* vaccine strain, composition, and/or vaccine as described herein. Instructions for use or for carrying out the methods described herein may also be provided in a kit. A kit may further include additional reagents, solvents, buffers, adjuvants, etc., required for carrying out the methods described herein. For example, a kit may comprise a lyophilization medium comprising: mannitol, a disaccharide selected from sucrose, trehalose, and a mixture of sucrose and trehalose, and gelatin in a weight ratio of about 1 mannitol:about 1 disaccharide:about 0.25 gelatin; a lyophilization medium comprising about 1% mannitol, about 1% disaccharide selected from sucrose, trehalose, and a mixture of sucrose and trehalose, and about 0.25% gelatin in phosphate buffer; a lyophilization medium comprising 1% mannitol, 1% sucrose, and 0.25% gelatin in 10 mM phosphate buffer pH 7.2; and/or the reagents mannitol, sucrose and/or trehalose, and gelatin in a weight ratio of about 1 mannitol:about 1 disaccharide (sucrose, trehalose, or a mixture of sucrose and trehalose):about 0.25 gelatin.

The technology described herein is not meant to be limited to particular methods, reagents, compounds, compositions or biological systems, which can, of course, vary. It should also be understood that terminology used herein is for the purpose of describing particular aspects only, and is not intended to be limiting.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the present technology.

General Procedures for Testing of Lyophilization Matrices.

For testing of lyophilization matrices in the Examples below, small volumes of $F.$ tularensis $\Delta$clpB mutants were grown in either Chamberlain's defined medium (CDM) (Chamberlain, R. E., Appl. Microbiol. 1965, 13: 232-5) or modified casein partial hydrolysate (MCPH) liquid medium (Karlsson, J. et al., Microb. Comp. Genomics 2000, 5(1): 25-39; Chamberlain, R. E., Appl. Microbiol. 1965, 13: 232-5). Cultures were then pelleted by centrifugation and re-suspended in an equal volume of various lyophilization matrices. For larger volumes (e.g., from 25 litres of SCHU S4 $\Delta$clpB grown in a fermenter), tangential flow filtration could be used to exchange growth medium with lyophilization matrix. Thereafter, $\Delta$clpB strains were lyophilized as follows:

Cultures of $\Delta$clpB were pelleted and resuspended in (an equal volume of) lyophilization matrix. Two mL aliquots were dispensed into 10 mL glass vials, and slotted rubber stoppers were placed loosely on top. The vials were placed on the shelves of the top chamber of a Lyph-Lock 6 Liter lyophilizer (Labconco, Kansas City, Mo.) at ambient temperature. Next, the temperature of the upper chamber was ramped down slowly from ambient temperature to −40° C. over 60-90 minutes. The temperature was held at −40° C. for 1 more hour to let the samples freeze. The vacuum pump was then turned on until the reading for the system stabilized (usually 5-10 M BAR×10$^{-3}$). The temperature of the upper chamber was then raised to −10° C. while the lower chamber remained at −40° C. The system was then run overnight for 18-19 hours under these conditions (primary drying). The next day the temperature of the upper chamber was adjusted to +20° C. over an approximately 45 minute period, then the samples were left to dry for another two hours (secondary drying). After secondary drying, the vials were sealed under vacuum by raising the bladder underneath the shelves of the upper chamber. The vacuum was turned off and vials to be stored were capped with metal caps. Samples were reconstituted with 2 mL of sterile water and plated on appropriate media to determine the viable bacterial count after lyophilization and storage for up to 3 years. This was compared to the viable bacterial count for the original re-suspension to determine the percentage loss after lyophilization.

As reported further below, the tested bacteria lost approximately 50% viability after lyophilization in 1% mannitol, 1% sucrose, 0.25% gelatin in 10 mM phosphate buffer, but thereafter remained stable for at least 1 year if stored at +4° C. or below, and for at least 3 years if stored at −20° C. or below. In contrast, the same lyophilized bacteria held at ambient temperature (22° C.) had lost essentially all viability by day 105 of storage. Additionally, we showed that diluting the bacteria by 100-fold preserved viability of ~50% immediately post-lyophilization and for at least 3 years thereafter.

Example 1

Viability of Various $F.$ tularensis Strains Following Lyophilization

First, a commercial lyophilization matrix called "Microbial Freeze Drying Buffer" (MFDB) from OPS Diagnostics LLC, NJ, was tested. MFDB is a general purpose lyophilization solution for use where high viability is not needed (e.g., for long-term storage of starter cultures), and is not suitable for clinical use. Nevertheless, it was tested to provide insight into the conditions needed to lyophilize live $F.$ tularensis vaccine strains with high viability after prolonged storage. MFDB was used with several attenuated strains of $F.$ tularensis and two different growth media (Table 1). As shown in Table 1, only SCHUS4$\Delta$clpB grown in modified casein partial hydrolysate medium (MCPH) and lyophilized in MFDB resulted in prolonged viability when stored at −80° C. All strains grown in Chamberlain's Defined Medium (CDM) survived lyophilization with unacceptably low viability.

TABLE 1

Viability of various F. tularensis strains following growth in CDM or MCPH and lyophilization in MFDB.

| Bacterium | Culture medium | Lyophilization matrix | % viability post-lyophilization[4] | Storage temperature | Storage period | % viability[4] |
|---|---|---|---|---|---|---|
| LVS[1] | CDM[2] 18 h | MFDB[3] | 6% | −80° C. | 28 days | 3.3% |
|  |  |  |  |  | 210 days | 3.4% |
| LVS | CDM 24 h | MFDB | 14.61% | −80° C. | N/A | NA |
| SCHU S4 $\Delta$ clpB | CDM 24 h | MFDB | 1.57% | −80° C. | N/A | NA |
| FSC043[5] | CDM 24 h | MFDB | 1.38% | −80° C. | N/A | N/A |
| LVS | CDM 24 h | MFDB | 6.46% | −80° C. | N/A | N/A |
| FSC043 | CDM 24 h | MFDB | 1.48% | −80° C. | N/A | N/A |
| SCHU S4 $\Delta$ clpB | MCPH[6] 24 h | MFDB | 51.92% | −80° C. | 11 days | 46.15% |
|  |  |  |  |  | 444 days | 31.92% |
| SCHU S4 $\Delta$ clpB | MCPH 18 h | MFDB | 48.28% | −80° C. −80° C. | N/A | N/A |

[1]F. tularensis live vaccine strain.
[2]CDM: Chamberlain's defined medium (liquid).
[3]MFDB: Commercial lyophilization matrix for bacteria in general.
[4]CFU count after reconstitution/CFU count pre-lyophilization x 100.
[5]FSC043: naturally attenuated strain of SCHU S4.
[6]MPCH: modified casein partial hydrolysate broth.

Since a lyophilization matrix not approved for human use could preserve the viability of SCHU S4ΔclpB, alternative matrices were examined using only clinically acceptable excipients. First 10% sucrose, 1.3% gelatin, 10 mM potassium phosphate was tested, as this mix was previously used for production of clinical LVS (Table 2). However, 10% sucrose, 1.3% gelatin did not give satisfactory survival of SCHU S4ΔclpB, nor did substituting sucrose with 5% mannitol (another common lyophilization excipient).

TABLE 2

Lyophilization of SCHU S4ΔclpB in sucrose or mannitol.

| Bacterium | Culture medium | Lyophilization matrix | % viability post-lyophilization[1] | Storage temperature | Storage period | % viability |
|---|---|---|---|---|---|---|
| SCHU S4 ΔclpB | MCPH 18 h | 10% sucrose, 1.3% gelatin | 8.89% | −80° C. | N/A | N/A |
| | | 5% mannitol-1.3% gelatin | 0.06% | | | |
| | | 5% mannitol | 1.72% | | | |

[1]CFU count after reconstitution/CFU count pre-lyophilization × 100.

Next we examined whether adding trehalose to the growth medium itself would improve survival after lyophilization (Table 3). Trehalose did not affect survival, although survival of bacteria grown solely in MCPH prior to lyophilization showed a 2-fold increase in viability compared to previous tests.

TABLE 3

Effect of adding trehalose to the growth medium on viability of SCHU S4ΔclpB after lyophilization.

| Bacterium | Culture medium | Lyophilization matrix 10 mM phosphate | % viability post-lyophilization[1] | Storage temperature | Storage period | % viability[1] |
|---|---|---|---|---|---|---|
| SCHU S4 ΔclpB | MCPH | 10% sucrose, 1.3% gelatin | 22.86 | −80° C. | N/A | N/A |
| | MPCH/ 3 mM trehalose | | 16.15% | | | |
| | MCPH | 10% sucrose, 1.3% gelatin, 3 mM trehalose | 14.12% | | | |
| | MPCH/ 3 mM trehalose | | 12.35% | | | |
| | MCPH | 10% sucrose, 1.3% gelatin, 10 mM trehalose | 14.19% | | | |
| | MPCH/ 3 mM trehalose | | 11.62% | | | |

[1]CFU count after reconstitution/CFU count pre-lyophilization × 100.

Next, various ratios of sucrose and mannitol were tested (Table 4). Altering the ratio of either sugar from 1% caused a noticeable decline in viability after lyophilization, with no obvious pattern.

TABLE 4

Effect of mannitol:sucrose ratio on viability of SCHU S4ΔclpB following lyophilization.

| Bacterium | Culture medium | Lyophilization matrix 10 mM phosphate + % mannitol: % sucrose | % viability post-lyophilization[1] | Storage temperature | Storage period | % viability[1] |
|---|---|---|---|---|---|---|
| SCHUS4 ΔclpB | MCPH | 1:1 | 27.08 | −80° C. | NA | N/A |
| | | 1:3 | 10.00 | | | |
| | | 1:5 | 13.33 | | | |
| | | 3:1 | 8.21 | | | |
| | | 3:3 | 7.10 | | | |
| | | 3:5 | 5.42 | | | |
| | | 5:1 | 5.71 | | | |
| | | 5:3 | 18.10 | | | |
| | | 5:5 | 10.80 | | | |

[1]CFU count after reconstitution/CFU count pre-lyophilization × 100.

Next, sucrose was replaced by trehalose (Table 5), as trehalose had been used by others for lyophilization and short-term storage of LVS. Altering either sugar to greater than 1% was detrimental to survival after lyophilization. Survival of SCHU S4ΔclpB with either 1% mannitol +1% sucrose or +1% trehalose was similar.

TABLE 5

Effect of mannitol: trehalose ratios on viability of SCHU S4ΔclpB following lyophilization.

| Bacterium | Culture medium | Lyophilization matrix 10 mM phosphate % mannitol: % trehalose | % viability post-lyophilization[1] | Storage temperature | Storage period | % viability[1] |
|---|---|---|---|---|---|---|
| SCHUS4 ΔclpB | MCPH | 1:1 | 30.48 | −80° C. | NA | N/A |
| | | 1:3 | 17.20 | | | |
| | | 1:5 | 9.33 | | | |
| | | 3:1 | 11.25 | | | |
| | | 3:3 | 11.43 | | | |
| | | 3:5 | 7.41 | | | |
| | | 5:1 | 4.75 | | | |
| | | 5:3 | 10.43 | | | |
| | | 5:5 | 9.50 | | | |

[1]CFU count after reconstitution/CFU count pre-lyophilization × 100.

The effect of adding gelatin to a lyophilization mixture of 1% mannitol:1% sucrose was tested, with varying amounts of gelatin. Gelatin had been used previously in two distinct preparations of LVS for human vaccination (Table 6).

TABLE 6

Effect of different gelatin concentrations on viability of SCHU S4ΔclpB after lyophilization.

| Bacterium | Culture medium | Lyophilization matrix 10 mM phosphate 1% mannitol: 1% sucrose + gelatin at: | % viability post-lyophilization[1] | Storage temperature | Storage period | % viability[1] |
|---|---|---|---|---|---|---|
| SCHUS4 ΔclpB | MCPH | 0% | 23.33 | −80° C. | NA | NA |
| | | 0.5% | 26.92 | | | |
| | | 1.0% | 16.67 | | | |
| | | 1.25% | 20.00 | | | |
| | | 1.5% | 15.38 | | | |

[1]CFU count after reconstitution/CFU count pre-lyophilization × 100.

Since lower amounts of gelatin appeared to preserve viability better, gelatin was tested in a lower range next (Table 7).

TABLE 7

Effect of very low concentrations of gelatin on viability of SCHU S4ΔclpB after lyophilization.

| Bacterium | Culture medium | Lyophilization matrix 10 mM phosphate 1% mannitol: 1% sucrose + gelatin at: | % viability post-lyophilization[1] | Storage temperature | Storage period | % viability[1] |
|---|---|---|---|---|---|---|
| SCHUS4 ΔclpB | MCPH | 0% | 41.82 | −80° C. | N/A | N/A |
| | | 0.1% | 38.15 | | | |
| | | 0.25% | 51.18 | | | |
| | | 0.5% | 31.54 | | | |
| | | 0.75% | 20.50 | | | |

[1]CFU count after reconstitution/CFU count pre-lyophilization × 100.

Next, it was determined whether time of harvest of SCHU S4 ΔclpB from flask growth in MCPH had an effect on viability following lyophilization and resuspension. In all cases, viability was greater in the presence than the absence of 0.25% gelatin (Table 8). This experiment was partially repeated using the 18 h and 21 h time points to harvest the ΔclpB from MCPH broth, with similar results of 55% viability (Table 9). The lyophilized material was at a concentration of ~1×10[10] CFU/ml, and it had to be diluted through 6-8 log$_{10}$ for manageable colony counts. Thus, the reported viabilities could be conservatively underestimated, given the potential for pipetting errors over such a large dilution range.

TABLE 8

Effect of gelatin and time of harvest on viability of SCHU S4ΔclpB after lyophilization.

| Bacterium | Culture medium | Lyophilization matrix 10 mM phosphate 1% mannitol: 1% sucrose +/− 0.25% gelatin | % viability post-lyophilization[1] | Storage temperature | Storage period | % viability[1] |
|---|---|---|---|---|---|---|
| SCHUS4 ΔclpB | MCPH | 18 h w/o gelatin | 25.0 | −80° C. | N/A | N/A |
| | | 18 h + gelatin | 41.4 | | | |
| | | 21 h w/o gelatin | 34.6 | | | |
| | | 21 h + gelatin | 60.1 | | | |
| | | 24 h w/o gelatin | 28.9 | | | |
| | | 24 h + gelatin | 45.3 | | | |

[1]CFU count after reconstitution/CFU count pre-lyophilization × 100.

TABLE 9

Effect of gelatin and time of harvest on viability of SCHU S4ΔclpB after lyophilization.

| Bacterium | Culture medium | Lyophilization matrix 10 mM phosphate 1% mannitol: 1% sucrose + 0.25% gelatin at: | % viability post-lyophilization[1] | Storage temperature | Storage period | % viability[1] |
|---|---|---|---|---|---|---|
| SCHUS4 ΔclpB | MCPH | 18 h w/o gelatin | 15.7 | −80° C. | N/A | N/A |
| | | 18 h + gelatin | 50.0 | | | |
| | | 21 h w/o gelatin | 28.2 | | | |
| | | 21 h + gelatin | 55.3 | | | |

[1]CFU count after reconstitution/CFU count pre-lyophilization × 100.

It is known that cold shocking suspensions of bacteria can enhance viability after lyophilization. Therefore, we determined whether this would make a difference in the presence or absence of gelatin or trehalose (Table 10). In this case, cold shocking was achieved by cooling for 1 h at +4° C. with stirring. Again, the addition of 0.25% gelatin to non-cold shocked bacteria re-suspended in 10 mM phosphate buffer containing 1% mannitol and 1% sucrose resulted in approximately 50% viability following lyophilization.

TABLE 10

Effect of cold shocking and addition of gelatin or trehalose on viability of SCHU S4 ΔclpB after lyophilization.

| Bacterium | Culture medium | Lyophilization matrix: 10 mM phosphate 1% mannitol:1% sucrose +/− 0.25% gelatin and/or trehalose and/or cold shock | % viability post-lyophilization[1] |
|---|---|---|---|
| SCHUS4 ΔclpB | MCHP, 21 h | No additives or cold shock | 34.3 |
| | | No cold shock + 0.25% gelatin | 50.7 |
| | | cold shock but no additives | 26.7 |
| | | Cold shock 0.25% gelatin | 43.9 |
| | | Cold shock 3 mM trehalose | 19.0 |
| | | Cold shock + 3 mM trehalose + 0.25% gelatin | 40.0 |

[1]CFU count after reconstitution/CFU count pre-lyophilization × 100.

Next, the need for 10 mM phosphate buffer in the lyophilization matrix was tested. As can be clearly seen, 10 mM phosphate buffer had a significant effect to preserve the viability of ΔclpB at all dilutions (Table 11).

TABLE 11

Effect of 10 mM phosphate buffer on viability of SCHU S4ΔclpB after lyophilization.

| Bacterium | Culture medium | Lyophilization matrix 1% mannitol: 1% sucrose + 0.25% gelatin at: | % viability post-lyophilization[1] | Storage temperature | Storage period | % viability[1] |
|---|---|---|---|---|---|---|
| SCHUS4 ΔclpB | MCPH, 21 h | neat 10 mM phosphate | 46.8 | −80° C. | N/A | N/A |
|  |  | water | 7.6 |  |  |  |
|  | 1:100 | 10 mM phosphate | 38.3 |  |  |  |
|  |  | water | <1% |  |  |  |
|  | 1:1000 | 10 mM phosphate | 22.0 |  |  |  |
|  |  | water | <1% |  |  |  |

[1]CFU count after reconstitution/CFU count pre-lyophilization × 100.

Next, lyophilized bacteria were grown in MCPH, pelleted by centrifugation and resuspended in 10 mM phosphate buffer containing 1% mannitol, 1% sucrose and 0.25% gelatin. These vials were stored at ambient (~22° C.), refrigerator (+4° C.), or freezer (−20° C. or −80° C.) temperatures. At various times, sample vials were thawed and viability determined as shown in FIG. 1. This experiment showed that SCHU S4ΔclpB could be stored for at least one year at +4° C. or colder and still retain essentially 100% of its original post-lyophilization viability when stored below freezing, or ~70% of its original post-lyophilization viability when stored at refrigeration temperature. The concentration of bacteria in this experiment was $2.0 \times 10^{10}$ CFU/ml, which represents about 400 human equivalent doses of LVS, an amount that is potentially acceptable for a vaccine developed for emergency use.

Figure 2:
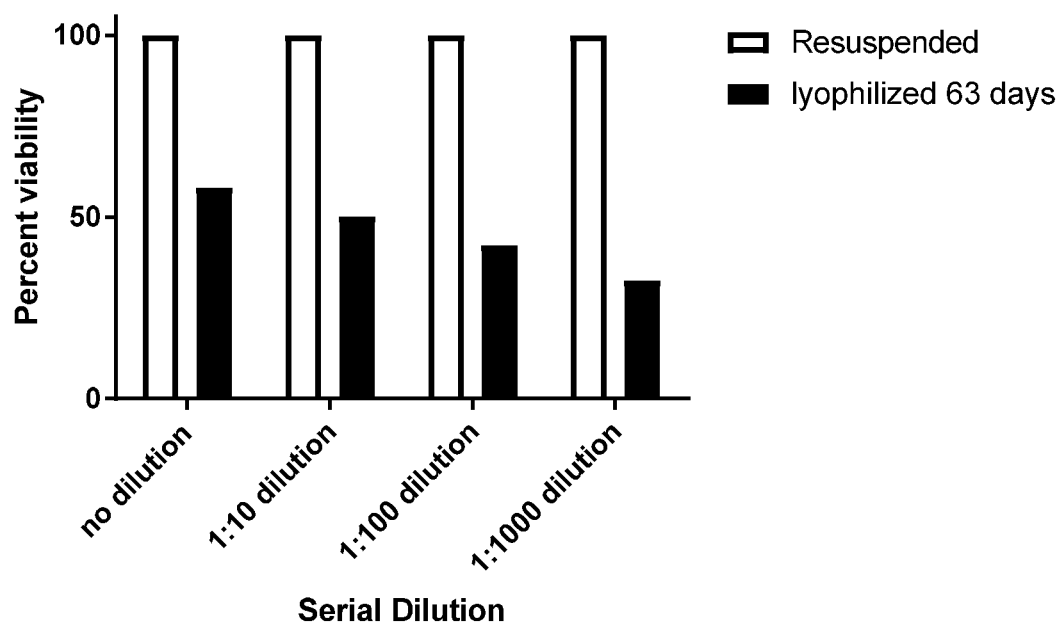
FIG. 2 shows percent viability of SCHU S4 ΔclpB resuspended in lyophilization medium, serially diluted as indicated, and plated before lyophilization, and 63 days after storage at −80° C. A modest decrease in viability at 63 days was observed with the more dilute vials, but even at 1:1000 dilution there was still ~70% retained viability after initial lyophilization.

It was then determined whether the aforementioned lyophilization procedure would work when the bacteria were diluted to a single dose/vial. The results are shown in FIG. 2. A modest decrease in viability at 63 days was observed with the more dilute vials, but even at 1:1000 dilution there was still ~70% retained viability after initial lyophilization.

It was next determined whether the optimized lyophilization matrix could be used for other strains of *F. tularensis*, beginning with *F. tularensis* strain LVS (Table 12). A side-by-side comparison of commerical lyophilization media (MFDB), lyophilization media having 1% mannitol, 1% sucrose, and 0.25% gelatin, and one of the original lyophilization mediums used for LVS (higher sucrose (10%) and gelatin (1.3%) but no mannitol) was performed (Table 12). Compared to LVS grown in Chamberlain's defined medium (Table 1), LVS grown in MCPH survived lyophilization much better in MFDB. However, its viability was lower than for SCHU S4 ΔclpB using the optimized lyophilization matrix.

TABLE 12

Ability of optimized lyophilization matrix to preserve viability of LVS.

| Bacterium | Culture medium | Lyophilization matrix 10 mM phosphate +: | % viability post-lyophilization[1] | Storage temperature | Storage period | % viability[1] |
|---|---|---|---|---|---|---|
| LVS | MCPH 21 h | MFDB | 63.3 | −80° C. | 364 days | 94.5 |
|  |  | 1% mannitol: 1% sucrose + 0.25% gelatin | 17.22 |  |  | 18.8 |
|  |  | 10% sucrose, 1.3% gelatin | 16.15 |  |  | 16.7 |

[1]CFU count after reconstitution/CFU count pre-lyophilization × 100.

To determine whether the same results would be obtained with other strains of *F. tularensis* subspecies *holarctica*, we repeated the above experiment with FSC200ΔclpB. For this strain, time of harvest appeared to have a major impact on survival of bacteria after lyophilization and resuspension (Table 13). Moreover, in this case MFDB performed poorly compared to the results obtained with LVS or FSC237ΔclpB.

TABLE 13

Ability of optimized lyophilization matrix to preserve viability of FSC200ΔclpB.

| Bacterium | Culture medium | Lyophilization matrix 10 mM phosphate +: | % viability post-lyophilization[1] | Storage temperature | Storage period | % viability[1] |
|---|---|---|---|---|---|---|
| FSC200 ΔclpB | MCPH 18 h | MFDB | 7.1 | −80° C. | NA | NA |
|  |  | 1% mannitol: 1% sucrose + 0.25% gelatin | 2.04 |  |  |  |
|  | MCPH 21 h | MFDB | 26.7 |  |  |  |
|  |  | 1% mannitol: 1% sucrose + 0.25% gelatin | 33.0 |  |  |  |

[1]CFU count after reconstitution/CFU count pre-lyophilization × 100.

Finally, it was determined whether the 10 mM phosphate lyophilization medium with 1% mannitol, 1% sucrose, and 0.25% gelatin, could be used on SCHU S4ΔclpB generated under standard manufacturing conditions. To this end, a 2.0 ml frozen stock was thawed and used to inoculate 1 litre of fresh MCPH broth in a 4 litre baffle flask. The flask was incubated for 18 h at 37° C. with shaking, and then 16.5 mL was transferred to a 25 litre fermenter containing 22 litres of fresh MCPH broth. After 22 h of controlled growth, 200 mL of SCHU S4ΔclpB was removed from the fermenter. 50 mL of this sample was pelleted by centrifugation, re-suspended in lyophilization matrix and freeze dried neat or at 1:100 dilution and held at +4° C., −20° C. or −80° C. for 3 years. At the highest storage temperature there was about a 50% loss in viability compared to the initial post-lyophilization viability, but at −20° C. and −80° C. storage temperatures, essentially 100% viability was retained (Table 14).

Figure 3:
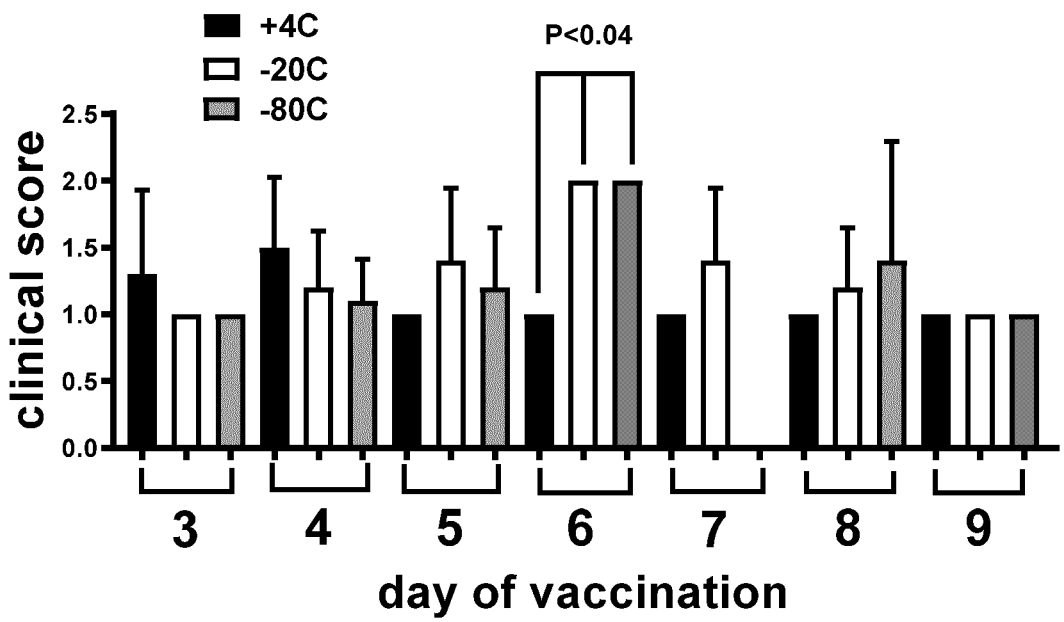
FIG. 3 shows clinical scores observed in BALB/c mice immunized intradermally with 1×10⁵ CFU of ΔclpB lyophilized for 3 years and stored at +4° C., −20° C., or −80° C. Clinical scores are determined as follows: 1=healthy; 2=slight pilo-erection; 3=slight pilo-erection and decreased mobility; 4=slight pilo-erection, decreased mobility, and hunching; 5=slight pilo-erection, decreased mobility, hunching, and shivering; 6=dead. ΔclpB stored at +4° C. appears to show somewhat reduced toxicity, but overall there were no significant differences in clinical score between animals vaccinated with ΔclpB lyophilized for 3 years and stored at +4° C., −20° C., or −80° C. * indicates a time point that was not scored, so data is unavailable.
Figure 4:
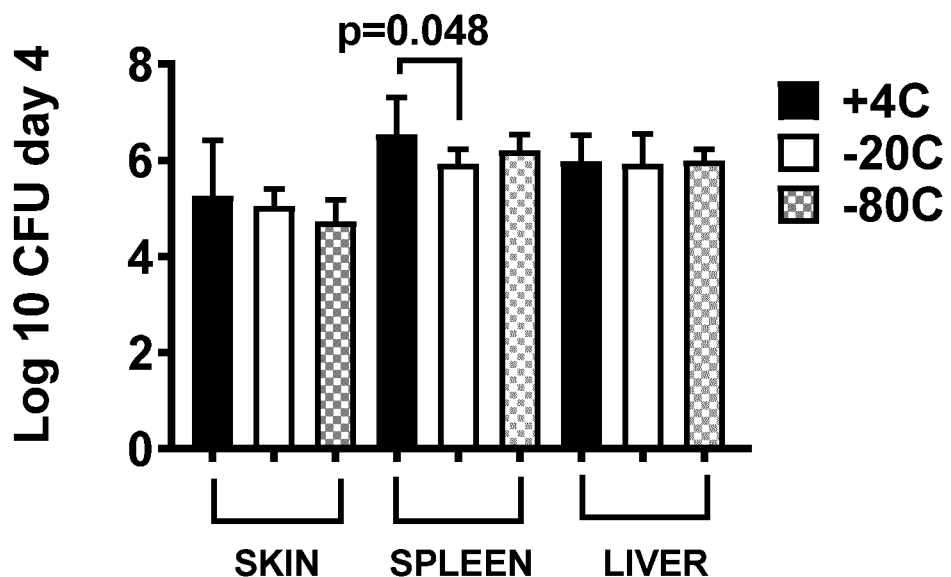
FIG. 4 shows levels of ΔclpB in tissues of BALB/c mice 4 days after intradermal immunization with 1×10⁵ CFU of ΔclpB lyophilized for 3 years and stored at +4° C., −20° C., or −80° C.
Figure 6:
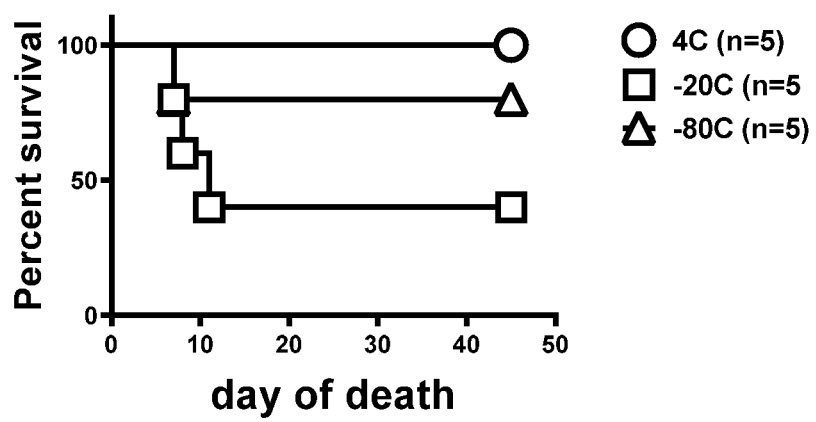
FIG. 6 shows survival of mice challenged intranasally with SCHU S4 bacteria, 6 weeks after intranasal immunization with 1×10⁴ CFU of ΔclpB lyophilized for 3 years and stored at +4° C., −20° C., or −80° C. The differences between survival curves were not statistically significant by the Mantel-Cox test.
Figure 7:
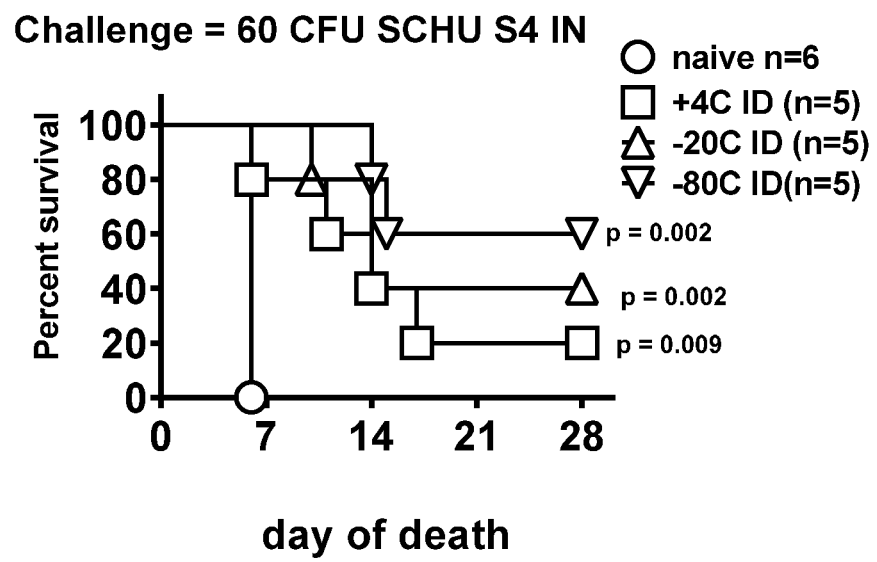
FIG. 7 shows survival of mice following intradermal immunization with 1×10⁵ CFU of ΔclpB lyophilized for 3 years and stored at +4° C., −20° C., or −80° C. and challenged intranasally (IN) with SCHU S4 six weeks later.
Figure 8:
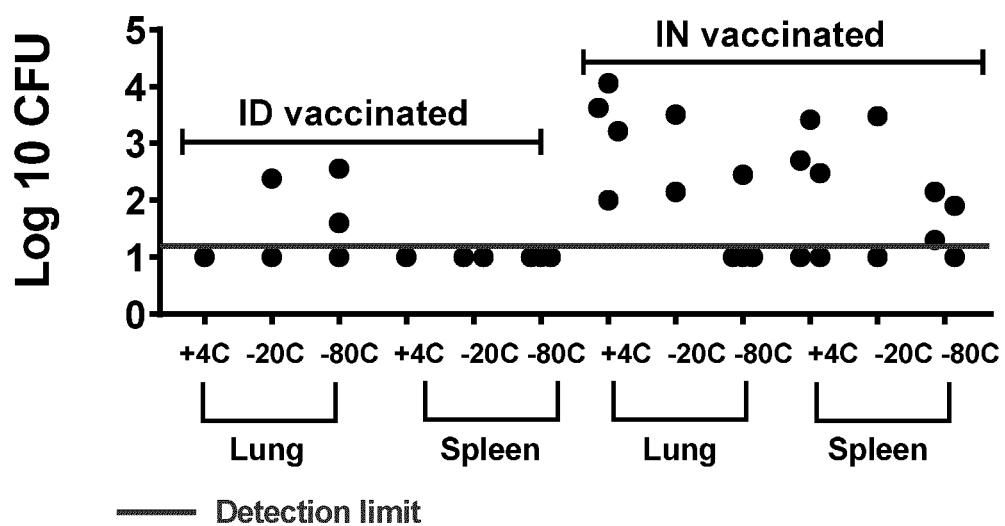
FIG. 8 shows the level of SCHU S4 bacteria remaining in the organs of mice following intradermal (ID) or intranasal (IN) immunization with 1×10⁵ CFU of ΔclpB lyophilized for 3 years and stored at +4° C., −20° C., or −80° C. and challenged with SCHU S4 six weeks later.

Moreover, all three vaccine preparations were identical in their safety and ability to protect mice from intranasal challenge with virulent strain SCHU S4 (FIGS. 3-8). FIG. 3 shows that storage of the vaccine for 3 years at any of the aforementioned three temperatures yielded similar clinical scores in BALB/c mice immunized ID with 1×10⁵ CFU. FIG. 4 shows the bacterial burdens of ΔclpB 4 days after ID vaccination with 1×10⁵ CFU. FIGS. 5A and 5B show the skin reactogenicity score at the site of injection of the mice depicted in FIG. 3. FIG. 6 shows that all three preparations of the vaccine stored for 3 years had similar lethality for BALB/c mice when given in a dose of 1×10⁴ CFU by the IN route. FIG. 7 shows that mice immunized ID with 1×10⁵ CFU of any one of the three vaccine preparations were equally protected from a subsequent IN challenge with 100 CFU of virulent strain SCHU S4 42 days later, while FIG. 8 shows that by 28 days after challenge the residual numbers of SCHU S4 in the target organs of the pathogen were also similar.

TABLE 14

Ability of optimized lyophilization matrix to preserve viability long-term.

| Bacterium | Culture medium | Lyophilization matrix | % viability post-lyophilization[1] | Storage temperature | Storage period | % viability[1] |
|---|---|---|---|---|---|---|
| SCHU S4ΔclpB | MCPH, fermenter 22 h neat | 1% mannitol:1% sucrose + 0.25% gelatin in 10 mM phosphate | 48.6 | +4° C. −20° C. −80° C. | 3 years | 41.9 123 138 |
| | MCPH fermenter 22 h 1:100 dilution | | 24.5 | +4° C. −20° C. −80° C. | 3 years | 50.3 138 133 |

[1]CFU count after storage/CFU count immediately post-lyophilization × 100.

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

The contents of all documents and references cited herein are hereby incorporated by reference in their entirety.

What is claimed is:

1. A lyophilization medium for freeze-drying a *Francisella tularensis* (*F. tularensis*) strain, wherein: the lyophilization medium comprises about 1% (w/v) of mannitol, about 1% (w/v) of a disaccharide, and about 0.25% (w/v) of gelatin in a phosphate buffer; wherein the disaccharide is selected from sucrose, trehalose, and a mixture of sucrose and trehalose; and *F. tularensis* wherein the *F. tularensis* strain is a mutant strain in which the clpB gene is inactivated, and wherein initial post-lyophilization viability of the *F. tularensis* strain is at least about 35% of the *F. tularensis* strain's pre-lyophilization viability.

2. The lyophilization medium of claim 1, wherein the medium comprises 1% (w/v) mannitol, 1% (w/v) sucrose, and 0.25% (w/v) gelatin in 10 mM phosphate buffer pH 7.2.

3. The lyophilization medium of claim 1, wherein the disaccharide is sucrose.

4. A method for lyophilizing a live vaccine strain of *Francisella tularensis* (*F. tularensis*) comprising the steps of: 1) pelleting a culture of the live vaccine strain by centrifugation; 2) resuspending the pelletized live vaccine strain in the lyophilization medium of claim 1 to form a suspension of the live vaccine strain in the lyophilization medium; and 3) freeze-drying the suspension.

5. A method for lyophilizing a live vaccine strain of *Francisella tularensis* (*F. tularensis*) suspended in a growth medium comprising the steps of: 1) replacing the growth medium with the lyophilization medium of claim 1 to obtain a suspension of the live vaccine strain in the lyophilization medium; and 2) freeze-drying the suspension.

6. The method of claim 5, wherein the growth medium is replaced with the lyophilization medium using filtration.

7. The method of claim 1, wherein the mutant strain is derived from a wild-type clinical strain of *F. tularensis* selected from the group consisting of SCHU S4, FSC033, FSC108, and FSC200.

8. The method of claim 6, wherein the filtration is tangential flow filtration.

9. A method for lyophilizing a live vaccine strain of *Francisella tularensis* (*F. tularensis*) comprising the steps of:
  1. thawing a concentrated frozen liquid preparation of the live vaccine strain comprising the lyophilization medium of claim 1; and
  2. freeze-drying the thawed preparation.

10. A method for lyophilizing a live vaccine strain of *Francisella tularensis* (*F. tularensis*) comprising the steps of:
  1. suspending the live vaccine strain in the lyophilization medium of claim 3; and
  2. freeze-drying the suspension.

11. A method for lyophilizing a live vaccine strain of *Francisella tularensis* (*F. tularensis*) comprising the steps of:
  1. suspending the live vaccine strain in the lyophilization medium of claim 4; and
  2. freeze-drying the suspension.

12. A composition comprising a lyophilization medium and a strain of *Francisella tularensis* (*F. tularensis*), wherein the lyophilization medium comprises about 1% (w/v) of mannitol, about 1% (w/v) of a disaccharide, and about 0.25% (w/v) of gelatin in a phosphate buffer; and wherein the disaccharide is selected from sucrose, trehalose, and a mixture of sucrose and trehalose and wherein initial post-lyophilization viability of the *F. tularensis* strain is at least about 35% of the *F. tularensis* strain's pre-lyophilization viability.

13. A lyophilizate of the composition of claim 12.

* * * * *